United States Patent
Bhirud et al.

(10) Patent No.: US 10,138,206 B2
(45) Date of Patent: Nov. 27, 2018

(54) AMORPHOUS FORM OF LOMITAPIDE MESYLATE

(71) Applicant: Glenmark Pharmaceuticals Limited, Mumbai (IN)

(72) Inventors: Shekhar Bhaskar Bhirud, Mumbai (IN); Samir Naik, Thane (IN); Sushanta Mishra, Bolangir (IN); Vipin Pandey, Thane (IN); Deepak S. Patekar, Navi Mumbai (IN)

(73) Assignee: GLENMARK PHARMACEUTICALS LIMITED, Mumbai (IN)

( * ) Notice: Subject to any disclaimer, the term of this patent is extended or adjusted under 35 U.S.C. 154(b) by 0 days.

(21) Appl. No.: 15/517,665

(22) PCT Filed: Oct. 6, 2015

(86) PCT No.: PCT/IB2015/057634
§ 371 (c)(1),
(2) Date: Apr. 7, 2017

(87) PCT Pub. No.: WO2016/055934
PCT Pub. Date: Apr. 14, 2016

(65) Prior Publication Data
US 2017/0305858 A1    Oct. 26, 2017

(30) Foreign Application Priority Data

Oct. 9, 2014   (IN) .......................... 3209/MUM/2014

(51) Int. Cl.
*C07D 211/58* (2006.01)
*A61K 31/4468* (2006.01)
*A61K 9/14* (2006.01)
*A61K 9/16* (2006.01)
*A61K 9/48* (2006.01)

(52) U.S. Cl.
CPC ............ *C07D 211/58* (2013.01); *A61K 9/143* (2013.01); *A61K 9/145* (2013.01); *A61K 9/146* (2013.01); *A61K 9/1623* (2013.01); *A61K 31/4468* (2013.01); *A61K 9/4866* (2013.01); *C07B 2200/13* (2013.01)

(58) Field of Classification Search
CPC ..................................................... C07D 211/58
USPC .......................................................... 546/203
See application file for complete search history.

(56) References Cited

U.S. PATENT DOCUMENTS

| | | | |
|---|---|---|---|
| 5,883,109 A | 3/1999 | Gregg et al. | |
| 6,087,511 A * | 7/2000 | Lin | C07D 207/34 548/517 |
| 6,528,660 B1 * | 3/2003 | Kumar | C07D 207/34 548/537 |
| 7,468,378 B2 | 12/2008 | Bertinato et al. | |
| 9,624,172 B2 * | 4/2017 | Parthasaradhi Reddy | C07D 211/58 |
| 2016/0083345 A1 * | 3/2016 | Desai | C07C 303/32 514/325 |

FOREIGN PATENT DOCUMENTS

| | | | |
|---|---|---|---|
| CN | 103690960 A | 4/2014 | |
| WO | 2015121877 A2 | 8/2015 | |
| WO | WO 2016012934 * | 1/2016 | ........... C07D 211/58 |

OTHER PUBLICATIONS

Hassar, Journal of the American Pharmacists Association, 53:6, 2013, 662-670.*
Chauhan, Journal of pharmaceutical sciences, vol. 102, 6, 2013.*
Bai, J.Y., "Lomitapide Mesylate", Chinese Journal of Medicinal Chemistry, vol. 23, No. 3, Jun. 30, 2013, p. 250.
Lojuxta Assessment Report, Aegerion Pharmaceutical Marketing Authorisation to the European Medicines Agency (EMA) for Lujuxta, Mar. 1, 2012.

* cited by examiner

*Primary Examiner* — Nizal S Chandrakumar
(74) *Attorney, Agent, or Firm* — Ryan, Mason & Lewis, LLP

(57) ABSTRACT

Provided is novel amorphous form of lomitapide mesylate salt and process for preparation thereof.

4 Claims, 2 Drawing Sheets

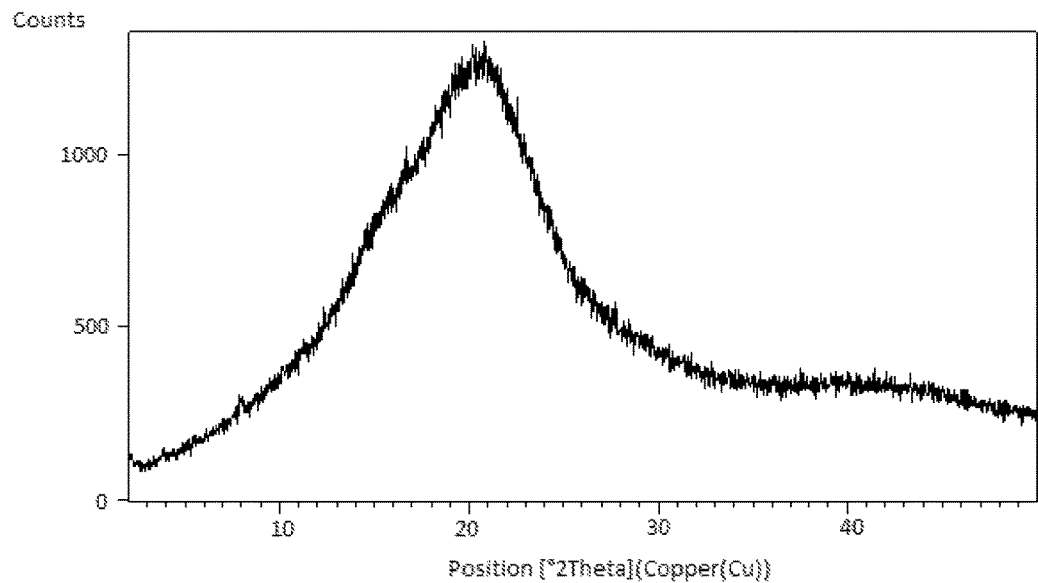
Figure 1: XRPD of amorphous form of lomitapide mesylate
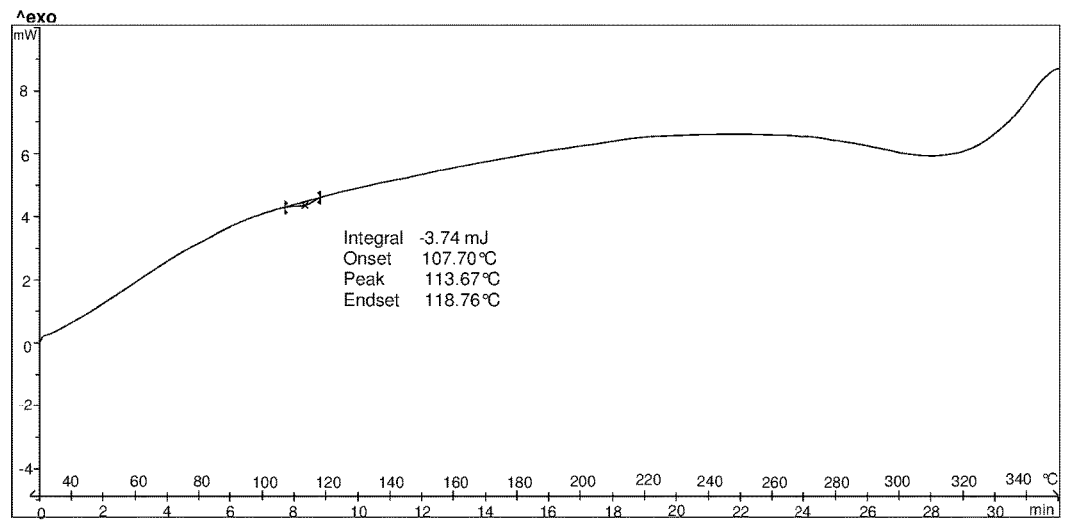
Figure 2: DSC thermogram of amorphous form of lomitapide mesylate

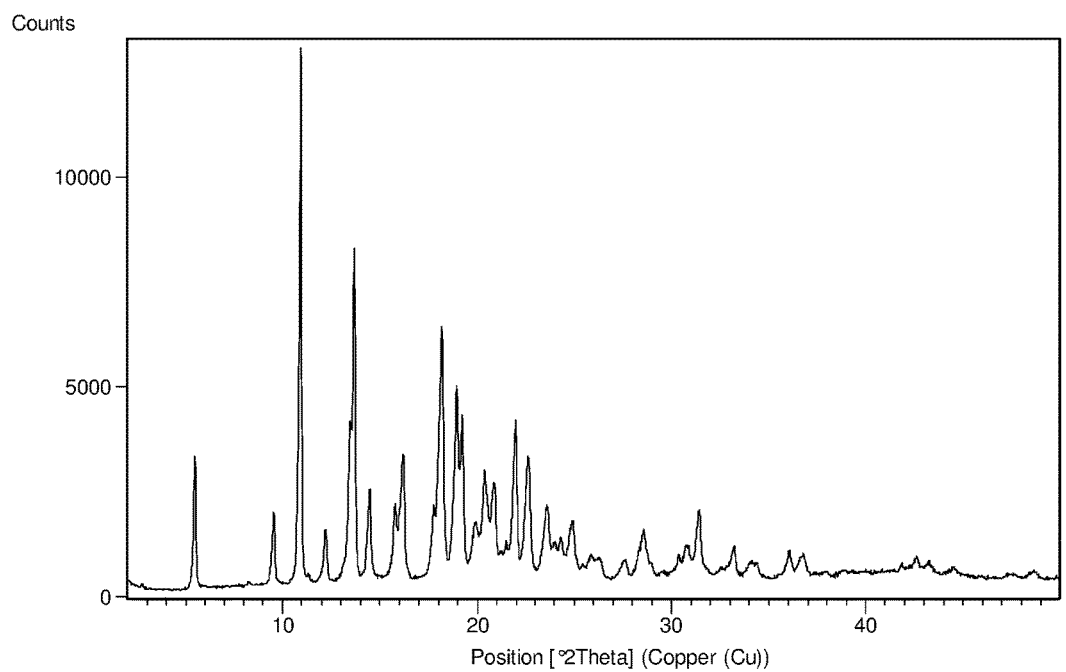
Figure 3: XRPD of lomitapide free base as per example 5.

AMORPHOUS FORM OF LOMITAPIDE MESYLATE

PRIORITY

This application claims priority under 35 U.S.C. § 371 to International Application No. PCT/IB2015/05634, filed Oct. 6, 2015 which claims the benefit of Indian Provisional Application 3209/MUM/2014 filed Oct. 9, 2014, and entitled "Amorphous Form of Lomitapide Mesylate", the contents of which are incorporated herein by reference.

FIELD OF THE INVENTION

The present invention relates to novel amorphous form of lomitapide mesylate salt and process for preparation thereof.

BACKGROUND OF THE INVENTION

Lomitapide mesylate is a microsomal triglyceride transfer protein inhibitor marketed as JUXTAPID® or LOJUXTA® in US and Europe respectively. It is represented by the following formula

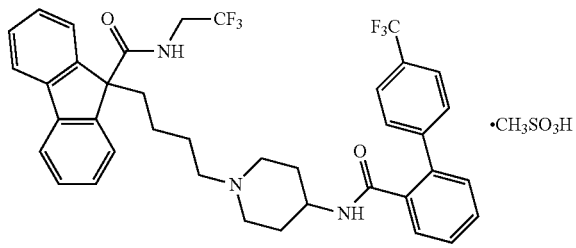

It is indicated as an adjunct to low fat diet to reduce low density lipoprotein cholesterol, total cholesterol, apolipoprotein B and nonhigh density lipoprotein cholesterol in patients with homozygous familial hypercholesterolemia.

The discovery of new amorphous forms of active pharmaceutical ingredients ("APIs") provides opportunities to improve the performance characteristics, the solubility, stability, flowability, tractability and compressibility of drug substances. Amorphous form of a drug provides solubility advantage as compared to the crystalline forms and hence offers opportunities for solubility and bioavailability enhancement.

The present invention provides novel amorphous form of lomitapide mesylate and process of preparation thereof.

Advantageously the amorphous lomitapide mesylate of the present invention does not contain genotoxic alkyl mesylate impurities like methyl mesylate and isopropyl mesylate.

SUMMARY OF THE INVENTION

In one aspect, the present invention provides novel amorphous form of lomitapide mesylate characterized by X-ray powder diffraction pattern which is substantially in accordance with FIG. 1.

In another aspect, present invention provides a process for preparation of amorphous form of lomitapide mesylate comprising
(a) providing a solution of lomitapide mesylate in a solvent;
(b) isolating the amorphous form of lomitapide mesylate by
  (i) removing the solvent from the solution obtained in (a); or
  (ii) combining the solution obtained in (a) with an antisolvent followed by optional cooling; or
  (iii) cooling the solution obtained in (a).

In another aspect, present invention provides a solid dispersion comprising amorphous form of lomitapide mesylate.

In another aspect, present invention provides a process for preparation of solid dispersion comprising amorphous form of lomitapide mesylate, comprising
(a) providing a mixture of lomitapide mesylate in combination with one or more pharmaceutically acceptable polymers and/or surfactants in a solvent;
(b) removing the solvent from the solution or suspension obtained in (a).

In another aspect, present invention provides a process for preparation of lomitapide mesylate, comprising
(a) treating lomitapide with methane sulfonic acid optionally in presence of a non hydroxylic solvent to obtain a reaction mixture; and
(b) isolating lomitapide mesylate from reaction mixture obtained in (a).

In another aspect, present invention provides lomitapide mesylate free of alkyl mesylates.

In another aspect, present invention provides a pharmaceutical composition comprising amorphous form of lomitapide mesylate together with one or more pharmaceutically acceptable carriers.

In another aspect, present invention provides a pharmaceutical composition comprising solid dispersion comprising amorphous form of lomitapide mesylate together with one or more pharmaceutically acceptable carriers.

BRIEF DESCRIPTION OF THE DRAWINGS

FIG. 1 is XRPD of amorphous form of lomitapide mesylate.

FIG. 2 is a DSC thermogram of amorphous form of lomitapide mesylate.

FIG. 3 is XRPD of lomitapide free base as per example 5.

DETAILED DESCRIPTION OF THE INVENTION

The present invention provides a novel amorphous form of lomitapide mesylate.

In one embodiment, the present invention provides an amorphous form of lomitapide mesylate characterized by X-ray powder diffraction pattern which is substantially in accordance with FIG. 1.

In one embodiment, the present invention provides an amorphous form of lomitapide mesylate characterized by differential scanning calorimetry endotherm curve, which is substantially in accordance with FIG. 2.

In one embodiment, the present invention provides amorphous form of lomitapide mesylate characterized by differential scanning calorimetry endotherm curve having an endothermic peak at about 113.0±3° C.

In one embodiment, the present invention provides an amorphous form of lomitapide mesylate characterized by water content of about 1-2% as measured by Karl Fischer method.

In one embodiment, the present invention provides amorphous lomitapide mesylate free of alkyl mesylates.

Alkyl mesylates include methyl mesylate, ethyl mesylate, isopropyl mesylate and the like.

"Free of alkyl mesylates", as used herein, means that alkyl mesylates are totally absent in amorphous lomitapide mesylate.

In one embodiment, the present invention provides amorphous lomitapide mesylate free of isopropyl mesylate.

"Free of isopropyl mesylate", as used herein, means that isopropyl mesylate is totally absent in amorphous lomitapide mesylate.

In one embodiment, the present invention provides amorphous lomitapide mesylate free of methyl mesylate.

"Free of methyl mesylate", as used herein, means that methyl mesylate is totally absent in amorphous lomitapide mesylate.

In one embodiment, the present invention provides amorphous lomitapide mesylate free of hydroxylic solvents.

"Free of hydroxylic solvents", as used herein, means that hydroxylic solvents are totally absent in amorphous lomitapide mesylate.

In one embodiment, the present invention provides lomitapide mesylate characterized by water content of about 1-2% as measured by Karl Fischer method.

In one embodiment, the present invention provides amorphous form of lomitapide mesylate having particle size distribution with D90 less than about 100 μm.

The present invention provides lomitapide mesylate as characterized and analyzed by following techniques:

A. X-ray powder diffraction profile was obtained using an X-ray Diffractometer (Philips X'Pert Pro, PANalytical). The measurements were carried out with a Pre FIX module programmable divergence slit and anti-scatter Slit (Offset 0.00°; target, Cu; filter, Ni; detector, X'Celerator [1]; Scanning Mode; Active length (2 Theta)=2.122°; generator 45 KV ; tube current 40 mAmp. The samples were scanned in the full 20 range of 2-50° with a "time-per-step" 50 seconds.

B. DSC (Mettler Toledo 822$^e$): Temperature range is "30° C. to 350° C." and heating rate is 10° C./minute.

C. Particle size analysis was performed on Malvern Mastersizer 2000 with Sample handling unit 'Scirocco 2000' using Air as dispersant.

D. Water determination, in the present invention, was done by Karl Fischer methodology using Karl Fischer titrator employing the following process:

The titration vessel was filled with the 15-20 ml of methanol. The start button was pressed. After the display shows 'drift OK', parameters were changed to 'KFT' mode and started. About 30.0 mg of water was added and the weight was entered and the start button was pressed. Burette reading was noted from the display after completion of the titration. K.F. Factor was calculated using the formula:

K.F. Factor=(weight of water in mg/Burette reading)

The instrument was then changed to 'KF mode'. The start button was pressed. About 100 mg of the test sample was transferred into the titration vessel and the sample weight was entered. Enter button was pressed. After completion of titration burette reading was noted from the display.

Water content of the test sample was calculated using the following equation:

$$\text{Water Content}(\%) = \frac{\text{Burette reading} \times \text{K.F. Factor}}{\text{Weight of sample in mg}} \times 100$$

In one embodiment, the present invention provides a substantially amorphous lomitapide mesylate.

As used herein, "substantially amorphous lomitapide mesylate" has less than about 30% crystalline lomitapide mesylate. In one embodiment, substantially amorphous lomitapide mesylate has less than about 25% crystalline lomitapide mesylate. In one embodiment, substantially amorphous lomitapide mesylate has less than about 15% crystalline lomitapide mesylate. In one embodiment, substantially amorphous lomitapide mesylate has less than about 10% crystalline lomitapide mesylate. Preferably, the substantially amorphous lomitapide mesylate has less than about 5% crystalline lomitapide mesylate.

The present invention provides a process for preparation of amorphous form of lomitapide mesylate comprising
  (a) providing a solution of lomitapide mesylate in a solvent; and
  (b) isolating the amorphous form of lomitapide mesylate by
    (i) removing the solvent from the solution obtained in (a); or
    (ii) combining the solution obtained in (a) with an antisolvent followed by optional cooling; or
    (iii) cooling the solution obtained in (a).

In one embodiment, providing a solution of lomitapide mesylate in a solvent in (a) comprises a solution obtained from reaction mixture in the final stage of process for preparation of lomitapide mesylate.

In one embodiment, providing a solution of lomitapide mesylate in a solvent in (a) comprises a solution obtained after dissolving lomitapide mesylate in a solvent.

Solvent used in (a) includes, but is not limited to esters such as methyl acetate, ethyl acetate, propyl acetate, butyl acetate, tert-butyl acetate and the like; haloalkanes such as methylene dichloride, ethylene dichloride, chloroform and the like; acyclic ethers such as diethyl ether, dimethyl ether, ethyl methyl ether, diisopropyl ether, methyl tertiary-butyl ether, and the like; cyclic ethers such as tetrahydrofuran, dioxane; alcohols such as methanol, ethanol, 1-propanol, 2-propanol, 1-butanol, 2-butanol, 1-pentanol and the like; ketones such as acetone, ethyl methyl ketone, methyl isobutyl ketone and the like; aliphatic hydrocarbons such as hexane, heptane, cyclohexane and the like; aromatic hydrocarbons such as toluene, xylene, chlorobenzene and the like; nitriles such as acetonitrile, propanenitrile and the like; dimethyl sulfoxide; dimethyl formamide; dimethyl acetamide; water; or mixtures thereof.

In one embodiment, the solvent may be selected from the group consisting of esters, haloalkanes, alcohols, ketones, cyclic ethers, nitriles, dimethyl sulfoxide; dimethyl formamide; dimethyl acetamide; and mixtures thereof. Preferably the solvent selected is ethyl acetate.

Removal of solvent in (b)(i) may be carried out by solvent distillation, concentration, spray drying, fluid bed drying, lyophilization, flash drying, spin flash drying, or thin-film drying.

In one embodiment, removal of solvent in (b)(i) may be carried out by solvent distillation, preferably under vacuum.

In one embodiment, the solvent distillation, preferably under vacuum, may be performed at a temperature of about 50-75° C. In one embodiment, the solvent distillation, preferably under vacuum, may be performed at a temperature of about 55-70° C., preferably at about 60-65° C.

In one embodiment, removal of solvent in (b)(i) may be carried out by spray drying.

In one embodiment, the spray drying is performed at a temperature of about 50-75° C. In one embodiment, spray drying may be performed at a temperature of about 55-70° C., preferably at about 60-65° C.

Antisolvent used in (b)(ii) is a solvent which on addition to a solution of lomitapide mesylate in (a) causes precipitation of lomitapide mesylate owing to insolubility of lomitapide mesylate in the solvent system generated. In one embodiment, the antisolvent used in b(ii) may include an acyclic ether such as diethyl ether, dimethyl ether, ethyl methyl ether, diisopropyl ether, methyl tertiary-butyl ether, and the like; an aliphatic hydrocarbon such as hexane, heptane, cyclohexane and the like; water; or mixtures thereof.

In one embodiment, the antisolvent used in b(ii) may be diisopropyl ether.

In one embodiment, the antisolvent used in b(ii) may be n-hexane or n-heptane.

In one embodiment, the antisolvent used in b(ii) may be water.

In one embodiment, the present invention provides a process for preparation of amorphous lomitapide mesylate wherein the solvent used in (a) is ethylacetate and the antisolvent used in b(ii) is diisopropyl ether.

In one embodiment, the present invention provides a process for preparation of amorphous lomitapide mesylate wherein the solvent used in (a) is ethylacetate and the antisolvent used in b(ii) is n-heptane.

In one embodiment, the present invention provides a process for preparation of amorphous lomitapide mesylate wherein the solvent used in (a) is ethylacetate and the antisolvent used in b(ii) is n-hexane.

After the addition of the antisolvent as in b(ii), optional cooling may be performed to obtain the precipitate.

In one embodiment, the present invention provides a process for preparation of amorphous form of lomitapide mesylate comprising
  (a) providing a solution of lomitapide mesylate in a solvent; and
  (b) isolating the amorphous form of lomitapide mesylate by cooling the solution obtained in (a) to a temperature of about −5 to 10° C.

In one embodiment, the present invention provides a process for preparation of amorphous form of lomitapide mesylate comprising
  (c) providing a solution of lomitapide mesylate in ethyl acetate; and
  (d) isolating the amorphous form of lomitapide mesylate by cooling the solution obtained in (a) to a temperature of about −5 to 10° C.

In one embodiment, the present invention provides a process for preparation of amorphous form of lomitapide mesylate comprising
  (a) providing a solution of lomitapide mesylate in a solvent; and
  (b) isolating the amorphous form of lomitapide mesylate by removing the solvent from solution obtained in (a) by solvent distillation under vacuum.

In one embodiment, the present invention provides a process for preparation of amorphous form of lomitapide mesylate comprising
  (a) providing a solution of lomitapide mesylate in ethyl acetate; and
  (b) isolating the amorphous form of lomitapide mesylate by removing ethyl acetate from solution obtained in (a) by solvent distillation under vacuum.

In one embodiment, the present invention provides a process for preparation of amorphous form of lomitapide mesylate comprising
  (a) providing a solution of lomitapide mesylate in a solvent; and
  (b) isolating the amorphous form of lomitapide mesylate by spray drying the solution obtained in (a).

In one embodiment, the present invention provides a process for preparation of amorphous form of lomitapide mesylate comprising
  (a) providing a solution of lomitapide mesylate in ethyl acetate; and
  (b) isolating the amorphous form of lomitapide mesylate by spray drying the solution obtained in (a).

In one embodiment, the present invention provides a process for preparation of amorphous form of lomitapide mesylate comprising
  (a) providing a solution of lomitapide mesylate in a solvent; and
  (b) isolating the amorphous form of lomitapide mesylate by combining the solution obtained in (a) with an antisolvent, followed by optional cooling.

In one embodiment, the present invention provides a process for preparation of amorphous form of lomitapide mesylate comprising
  (a) providing a solution of lomitapide mesylate in ethyl acetate; and
  (b) isolating the amorphous form of lomitapide mesylate by combining the solution obtained in (a) with an antisolvent, followed by optional cooling.

In one embodiment, the present invention provides a process for preparation of amorphous form of lomitapide mesylate comprising
  (a) providing a solution of lomitapide mesylate in ethyl acetate; and
  (b) isolating the amorphous form of lomitapide mesylate by combining the solution obtained in (a) with diisopropyl ether or n-heptane, followed by optional cooling.

In one embodiment, the amorphous lomitapide mesylate obtained in (b) may, optionally, be filtered and dried. Drying may be performed at a temperature of about 55-110° C. Drying may be performed preferably in the presence of vacuum.

In one embodiment, drying may be performed under vacuum at a temperature of about 55-70° C., preferably at a temperature of about 60-65° C.

In one embodiment, drying may be performed under vacuum at a temperature of about 100-110° C., preferably at a temperature of about 105° C.

In one embodiment, the present invention provides a process wherein lomitapide mesylate in (a), as described above, may be prepared by treating lomitapide with methane sulfonic acid, optionally in presence of a solvent.

Solvent used in (a) are as discussed supra.

In one embodiment, the present invention provides a process for preparation of amorphous form of lomitapide mesylate comprising treating lomitapide with methane sulfonic acid in presence of a solvent and isolating the amorphous form of lomitapide mesylate by filtration of the reaction mixture. Solvent used in (a) are as discussed supra.

In one embodiment, the amorphous lomitapide mesylate obtained after filtration may be dried by method as discussed supra.

In one embodiment, the present invention provides a process for preparation of amorphous lomitapide mesylate free of alkyl mesylates comprising treating lomitapide with methanesulfonic acid optionally in presence of a non hydroxylic solvent. The amorphous lomitapide mesylate, so obtained, is free of alkyl mesylates, known to be genotoxic compounds, which form if the mesylate salt is prepared in the presence of hydroxylic solvents.

In one embodiment, the present invention provides a process for preparation of amorphous lomitapide mesylate free of alkyl mesylates comprising treating lomitapide with methanesulfonic acid in presence of a non hydroxylic solvent. The amorphous lomitapide mesylate, so obtained, is free of alkyl mesylates, known to be genotoxic compounds, which form if the mesylate salt is prepared in the presence of hydroxylic solvents.

The non hydroxylic solvent is any solvent which does not have alcohol. The non hydroxylic solvents used may be selected from esters such as methyl acetate, ethyl acetate, propyl acetate, butyl acetate, tert-butyl acetate and the like; haloalkanes such as methylene dichloride, ethylene dichloride, chloroform and the like; acyclic ethers such as diethyl ether, dimethyl ether, ethyl methyl ether, diisopropyl ether, methyl tertiary-butyl ether, and the like; cyclic ethers such as tetrahydrofuran, dioxane; ketones such as acetone, ethyl methyl ketone, methyl isobutyl ketone and the like; aliphatic hydrocarbons such as hexane, heptane, cyclohexane and the like; aromatic hydrocarbons such as toluene, xylene, chlorobenzene and the like; nitriles such as acetonitrile, propanenitrile and the like; dimethyl sulfoxide; dimethyl formamide; dimethyl acetamide; water; or mixtures thereof.

In one embodiment, the non hydroxylic solvent may be selected from the group consisting of esters, haloalkanes, ketones, cyclic ethers, nitriles, dimethyl sulfoxide; dimethyl formamide; dimethyl acetamide; and mixtures thereof. In one embodiment, the solvent used may be an ester, preferably ethyl acetate.

In one embodiment the present invention provides a process for preparation of amorphous form of lomitapide mesylate, free of alkyl mesylates comprising
  (a) providing a solution of lomitapide mesylate in a non hydroxylic solvent; and
  (b) isolating the amorphous form of lomitapide mesylate by
    (i) removing the non hydroxylic solvent from the solution obtained in (a); or
    (ii) combining the solution obtained in (a) with a non hydroxylic antisolvent followed by optional cooling; or (iii) cooling the solution obtained in (a).

The non hydroxylic solvents used may be selected from esters such as methyl acetate, ethyl acetate, propyl acetate, butyl acetate, tert-butyl acetate and the like; haloalkanes such as methylene dichloride, ethylene dichloride, chloroform and the like; acyclic ethers such as diethyl ether, dimethyl ether, ethyl methyl ether, diisopropyl ether, methyl tertiary-butyl ether, and the like; cyclic ethers such as tetrahydrofuran, dioxane; ketones such as acetone, ethyl methyl ketone, methyl isobutyl ketone and the like; aliphatic hydrocarbons such as hexane, heptane, cyclohexane and the like; aromatic hydrocarbons such as toluene, xylene, chlorobenzene and the like; nitriles such as acetonitrile, propanenitrile and the like; dimethyl sulfoxide; dimethyl formamide; dimethyl acetamide; water; or mixtures thereof.

Non hydroxylic antisolvent used in (b)(ii) is a solvent which on addition to a solution of lomitapide mesylate in (a) causes precipitation of lomitapide mesylate owing to insolubility of lomitapide mesylate in the solvent system generated. In one embodiment, the non hydroxylic antisolvent used in b(ii) may include an acyclic ether such as diethyl ether, dimethyl ether, ethyl methyl ether, diisopropyl ether, methyl tertiary-butyl ether, and the like; an aliphatic hydrocarbon such as hexane, heptane, cyclohexane and the like; water; or mixtures thereof.

In one embodiment the present invention provides a process for preparation of amorphous form of lomitapide mesylate, free of alkyl mesylates comprising
  (a) providing a solution of lomitapide mesylate in ester solvent; and
  (b) isolating the amorphous form of lomitapide mesylate by combining the solution obtained in (a) with a non hydroxylic antisolvent followed by optional cooling;

In one embodiment the non hydroxylic antisolvent is an aliphatic hydrocarbon such as hexane, heptane, cyclohexane and the like.

In one embodiment, present invention provides a process for the preparation of lomitapide comprising crystallizing lomitapide from a solvent selected from the group consisting of alcohols, water or mixtures thereof.

In one embodiment, present invention provides a process for the preparation of lomitapide comprising crystallizing lomitapide from a mixture of ethanol and water.

In one aspect, in above process, solvent used for the crystallization of lomitapide is a mixture of ethanol and water having ratio 7:3.

The present invention provides a solid dispersion comprising amorphous form of lomitapide mesylate.

In one embodiment, present invention provides a solid dispersion comprising amorphous form of lomitapide mesylate further comprising one or more pharmaceutically acceptable carriers. Pharmaceutically acceptable carriers may be selected from polymers, surfactants or inert pharmaceutically acceptable substances.

In one embodiment, present invention provides a solid dispersion comprising amorphous form of lomitapide mesylate further comprising one or more pharmaceutically acceptable polymers and/or surfactants.

The polymer, used in the solid dispersion includes, but is not limited to cellulose derivatives (eg HPMC, HPMCE15, HPMC E50, HPC, ethyl cellulose, CMC-Na, cellulose acetate trimellitate (CAT), hydroxypropylcellulose acetate phthalate (HPCAP), hydroxypropylmethyl-cellulose acetate phthalate (HPMCAP), methylcellulose acetate phthalate (MCAP), cellulose acetate phthalate (CAP)), polyvinyl pyrrolidones, polyethylene glycols, polyvinyl alcohols, acrylates (eg polymethacrylate—Eudragit® E and S), cross-linked polyacrylic acid (carbopol), cyclodextrins (α-cyclodextrins, (β-cyclodextrins, γ-cyclodextrins, hydroxyl-propyl β-cyclodextrins), polyoxyalkylenes, polyethylene oxides, copolymers (eg polyvinylpyrrolidone-vinylacetate (PVP-VA) copolymer), and derivatives thereof.

The surfactant, used in the solid dispersion includes, but is not limited to sorbitan fatty acid esters (e.g., Spans®), polyoxyethylene sorbitan fatty acid esters (e.g., Tweens®), sodium lauryl sulfate (SLS), sodium dodecylbenzene sulfonate (SDBS) dioctyl sodium sulfosuccinate (Docusate), dioxycholic acid sodium salt (DOSS), Sorbitan Monostearate, Sorbitan Tristearate, hexadecyltrimethyl ammonium bromide (HTAB), Sodium N-lauroylsarcosine, Sodium Oleate, Sodium Myristate, Sodium Stearate, Sodium Palmitate, Gelucire 44/14, ethylenediamine tetraacetic acid (EDTA), Vitamin E d-alpha tocopheryl polyethylene glycol 1000 succinate (TPGS), Lecithin, MW 677-692, Glutanic acid monosodium monohydrate, Labrasol, PEG 8 caprylic/capric glycerides, Transcutol, diethylene glycol monoethyl ether, Solutol HS-15, polyethylene glycol/hydroxystearate, Taurocholic Acid, Pluronic F68, Pluronic F108, and Pluronic F127 (or any other polyoxyethylene-polyoxypropylene co-polymers (Pluronics®) or saturated polyglycolized glycerides (Gelucirs®)).

Other pharmaceutically acceptable carriers used may include gelatines, ovalbumin, soybean proteins, sugar alcohols, non-sucrose fatty acid esters, starches, modified starches, polycarbophil, lactose, Isomalt, gum arabic, sodium alginate, xantham gum, carraageenan, locust bean gum (ceratonia), chitosan, guar gum, cross-linked high amylase starch.

The present invention provides a process for preparation of solid dispersion comprising amorphous form of lomitapide mesylate comprising
(a) providing a mixture of lomitapide mesylate in combination with one or more pharmaceutically acceptable carriers in a solvent; and
(b) removing the solvent from the solution or suspension obtained in (a).

The present invention provides a process for preparation of solid dispersion comprising amorphous form of lomitapide mesylate comprising
(a) providing a mixture of lomitapide mesylate in combination with one or more pharmaceutically acceptable polymers and/or surfactants in a solvent; and
(b) removing the solvent from the solution or suspension obtained in (a).

Solvent used in (a) includes, but is not limited to esters such as methyl acetate, ethyl acetate, propyl acetate, butyl acetate, tert-butyl acetate and the like; haloalkanes such as methylene dichloride, ethylene dichloride, chloroform and the like; acyclic ethers such as diethyl ether, dimethyl ether, ethyl methyl ether, diisopropyl ether, methyl tertiary-butyl ether, and the like; cyclic ethers such as tetrahydrofuran, dioxane; alcohols such as methanol, ethanol, 1-propanol, 2-propanol, 1-butanol, 2-butanol, 1-pentanol and the like; ketones such as acetone, ethyl methyl ketone, methyl isobutyl ketone and the like; aliphatic hydrocarbons such as hexane, heptane, cyclohexane and the like; aromatic hydrocarbons such as toluene, xylene, chlorobenzene and the like; nitriles such as acetonitrile, propanenitrile and the like; dimethyl sulfoxide; dimethyl formamide; dimethyl acetamide; water; or mixtures thereof.

In one embodiment, the solvent may be selected from the group consisting of esters, haloalkanes, alcohols, ketones, cyclic ethers, nitriles, dimethyl sulfoxide; dimethyl formamide; dimethyl acetamide; and mixtures thereof. Preferably the solvent selected is ethyl acetate.

Removal of solvent in (b) may be carried out by solvent distillation, concentration, spray drying, fluid bed drying, lyophilization, flash drying, spin flash drying, or thin-film drying. In one embodiment, the present invention provides a process wherein lomitapide mesylate in (a), may be prepared by treating lomitapide with methane sulfonic acid, optionally in presence of a solvent. Solvent used is as discussed supra.

The present invention provides a process for preparation of lomitapide mesylate comprising
(a) treating lomitapide with methane sulfonic acid optionally in presence of a solvent to obtain a reaction mixture; and
(b) isolating lomitapide mesylate from reaction mixture obtained in (a)

The isolation in (b) may be carried out either by filtration of the reaction mixture obtained in (a) to separate the lomitapide mesylate from the reaction mixture; or by precipitating out lomitapide mesylate from the reaction mixture obtained in (a) by addition of an antisolvent to it optionally followed by cooling; or by removing the solvent from the reaction mixture obtained in (a); or by cooling the reaction mixture obtained in (a).

In one embodiment, the solvent used in (a) may be a non hydroxylic solvent. The non-hydroxylic solvents used in (a) may be selected from esters such as methyl acetate, ethyl acetate, propyl acetate, butyl acetate, tert-butyl acetate and the like; haloalkanes such as methylene dichloride, ethylene dichloride, chloroform and the like; acyclic ethers such as diethyl ether, dimethyl ether, ethyl methyl ether, diisopropyl ether, methyl tertiary-butyl ether, and the like; cyclic ethers such as tetrahydrofuran, dioxane; ketones such as acetone, ethyl methyl ketone, methyl isobutyl ketone and the like; aliphatic hydrocarbons such as hexane, heptane, cyclohexane and the like; aromatic hydrocarbons such as toluene, xylene, chlorobenzene and the like; nitriles such as acetonitrile, propanenitrile and the like; dimethyl sulfoxide; dimethyl formamide; dimethyl acetamide; water; or mixtures thereof.

In one embodiment, the solvent may be selected from the group consisting of esters, haloalkanes, ketones, cyclic ethers, nitriles, dimethyl sulfoxide; dimethyl formamide; dimethyl acetamide; and mixtures thereof. In one embodiment, the solvent used may be an ester, preferably ethyl acetate.

Removal of solvent from the reaction mixture for isolating lomitapide mesylate may be carried out by solvent distillation or concentration.

In one embodiment, removal of solvent may be carried out by solvent distillation, preferably under vacuum.

In one embodiment, the solvent distillation, preferably under vacuum, may be performed at a temperature of about 50-75° C. In one embodiment, the solvent distillation, preferably under vacuum, may be performed at a temperature of about 55-70° C., preferably at about 60-65° C.

In one embodiment, antisolvent used for isolating lomitapide are as discussed supra.

In one embodiment, the antisolvent used may include an acyclic ether such as diethyl ether, dimethyl ether, ethyl methyl ether, diisopropyl ether, methyl tertiary-butyl ether, and the like; an aliphatic hydrocarbon such as hexane, heptane, cyclohexane and the like; water; or mixtures thereof.

In one embodiment, the antisolvent used may be diisopropyl ether.

In one embodiment, the antisolvent used may be n-hexane or n-heptane.

In one embodiment, the antisolvent used may be water.

In one embodiment, the solvent used in (a) is ethylacetate and the antisolvent used is diisopropyl ether.

In one embodiment, the solvent used in (a) is ethylacetate and the antisolvent used is n-heptane.

In one embodiment, the solvent used in (a) is ethylacetate and the antisolvent used is n-hexane.

The present invention provides a process for preparation of lomitapide mesylate comprising
(a) treating lomitapide with methane sulfonic acid in presence of a solvent to obtain a reaction mixture; and
(b) isolating lomitapide mesylate from reaction mixture obtained in (a) by addition of an antisolvent to it or by addition of reaction mixture obtained in (a) to the antisolvent; optionally followed by cooling.

After the addition of the antisolvent or addition of reaction mixture to antisolvent, optional cooling may be performed to obtain the precipitate.

In one embodiment, cooling of the reaction mixture obtained in (a) involves cooling to a temperature of −5 to 10° C., preferably 0-5° C.

The present invention provides a process for preparation of lomitapide mesylate comprising
(a) treating lomitapide with methane sulfonic acid optionally in presence of a solvent to obtain a reaction mixture; and
(b) isolating lomitapide mesylate from reaction mixture obtained in (a) by cooling the reaction mixture obtained in (a).

The present invention provides a process for preparation of lomitapide mesylate comprising
(a) treating lomitapide with methane sulfonic acid optionally in presence of ethyl acetate to obtain a reaction mixture; and
(b) isolating lomitapide mesylate from reaction mixture obtained in (a) by cooling the reaction mixture obtained in (a).

In one embodiment, the present invention provides a process for preparation of lomitapide mesylate comprising
(a) treating lomitapide with methane sulfonic acid optionally in presence of a solvent to obtain a reaction mixture; and
(b) isolating lomitapide mesylate from reaction mixture obtained in (a) by cooling the reaction mixture obtained in (a) to a temperature of about −5 to 10° C.

The present invention provides a process for preparation of lomitapide mesylate comprising
(a) treating lomitapide with methane sulfonic acid optionally in presence of a solvent to obtain a reaction mixture; and
(b) isolating lomitapide mesylate from reaction mixture obtained in (a) by solvent distillation under vacuum.

The present invention provides a process for preparation of lomitapide mesylate comprising
(a) treating lomitapide with methane sulfonic acid optionally in presence of ethyl acetate to obtain a reaction mixture; and
(b) isolating lomitapide mesylate from reaction mixture obtained in (a) by solvent distillation under vacuum.

In one embodiment, the present invention provides a process for preparation of lomitapide mesylate comprising
(a) treating lomitapide with methane sulfonic acid in presence of ethyl acetate to obtain a reaction mixture; and
(b) isolating lomitapide mesylate from reaction mixture obtained in (a) by addition of an antisolvent to it or by addition of reaction mixture obtained in (a) to the antisolvent; optionally followed by cooling.

In one embodiment, the lomitapide mesylate obtained in (b) may, optionally, be filtered and dried. Drying may be performed at a temperature of about 55-110° C. Drying may be performed preferably in the presence of vacuum. In one embodiment, drying may be performed under vacuum at a temperature of about 55-70° C., preferably at a temperature of about 60-65° C. In one embodiment, drying may be performed under vacuum at a temperature of about 100-110° C., preferably at a temperature of about 105° C.

In one embodiment, the present invention provides lomitapide mesylate free of alkyl mesylates.

Alkyl mesylates include methyl mesylate, ethyl mesylate, isopropyl mesylate and the like.

"Free of alkyl mesylates", as used herein, means that alkyl mesylates are totally absent in lomitapide mesylate.

In one embodiment, the present invention provides lomitapide mesylate free of hydroxylic solvents.

"Free of hydroxylic solvents", as used herein, means that hydroxylic solvents are totally absent in lomitapide mesylate.

In one embodiment, the present invention provides a process for preparation of lomitapide mesylate free of alkyl mesylates comprising treating lomitapide with methanesulfonic acid in presence of a non hydroxylic solvent. The lomitapide mesylate, so obtained, is free of alkyl mesylates, known to be genotoxic compounds, which form if the mesylate salt is prepared in the presence of hydroxylic solvents.

The non-hydroxylic solvents used may be selected from esters such as methyl acetate, ethyl acetate, propyl acetate, butyl acetate, tert-butyl acetate and the like; haloalkanes such as methylene dichloride, ethylene dichloride, chloroform and the like; acyclic ethers such as diethyl ether, dimethyl ether, ethyl methyl ether, diisopropyl ether, methyl tertiary-butyl ether, and the like; cyclic ethers such as tetrahydrofuran, dioxane; ketones such as acetone, ethyl methyl ketone, methyl isobutyl ketone and the like; aliphatic hydrocarbons such as hexane, heptane, cyclohexane and the like; aromatic hydrocarbons such as toluene, xylene, chlorobenzene and the like; nitriles such as acetonitrile, propanenitrile and the like; dimethyl sulfoxide; dimethyl formamide; dimethyl acetamide; water; or mixtures thereof.

In one embodiment, the solvent may be selected from the group consisting of esters, haloalkanes, ketones, cyclic ethers, nitriles, dimethyl sulfoxide; dimethyl formamide; dimethyl acetamide; and mixtures thereof. In one embodiment, the solvent used may be an ester, preferably ethyl acetate.

In one embodiment, the present invention provides amorphous form of lomitapide mesylate free of alkyl mesylates. Alkyl mesylates include methyl mesylate, ethyl mesylate, isopropyl mesylate and the like.

"Free of alkyl mesylates", as used herein, means that alkyl mesylates are totally absent in amorphous form of lomitapide mesylate.

In one embodiment, the present invention provides amorphous form of lomitapide mesylate free of hydroxylic solvents.

"Free of hydroxylic solvents", as used herein, means that hydroxylic solvents are totally absent in amorphous form of lomitapide mesylate.

In one embodiment, the content of alkyl mesylate in lomitapide mesylate or amorphous lomitapide mesylate was determined by GCMS with conditions as described below.

Apparatus: Gas Chromatograph quipped with autosampler.

Column: DB-624, 30 m×0.32 mmID, 1.8 μm+MSCAP, 1.44 m×0.180 mmID

Column Temperature: 100° C. (hold for 5.0 minutes) to 230° C. @30° C./minute hold at 230° C. for 15 minutes Injector: 220° C.

Carrier gas: Helium

Linear Velocity: 30 cm/sec

Flow: 1.6075 ml/min

Split Ratio: (6:1)

Diluent: Methanol

Injection Volume: 1.0 μL

In one embodiment, the present invention provides lomitapide mesylate characterized by water content of about 1-2% as measured by Karl Fischer method.

In one embodiment, the present invention provides lomitapide mesylate wherein the level of one or more impurities represented by formulas A, B, C, D, E, F, G, H, I, J, K, L and M is less than about 0.15% w/w with respect to lomitapide mesylate as measured by HPLC.

| Structure | Impurity |
|---|---|
| 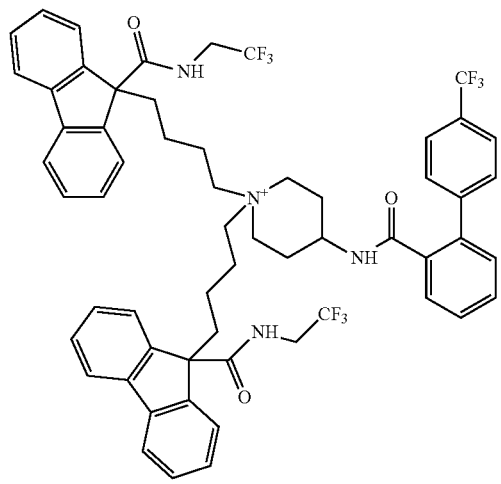 [SMILES: O=C(NC1CC[N+](CCCCC2(C(=O)NCC(F)(F)F)c3ccccc3-c3ccccc32)(CCCCC2(C(=O)NCC(F)(F)F)c3ccccc3-c3ccccc32)CC1)c1ccccc1-c1ccc(C(F)(F)F)cc1] | A |
| 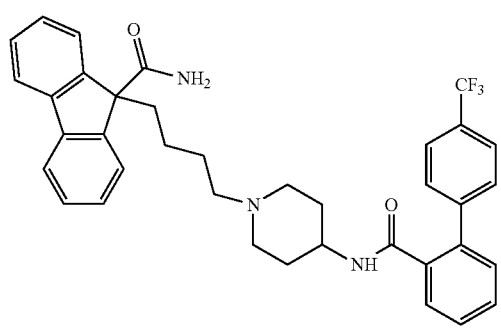 [SMILES: NC(=O)C1(CCCCN2CCC(NC(=O)c3ccccc3-c3ccc(C(F)(F)F)cc3)CC2)c2ccccc2-c2ccccc21] | B |
| 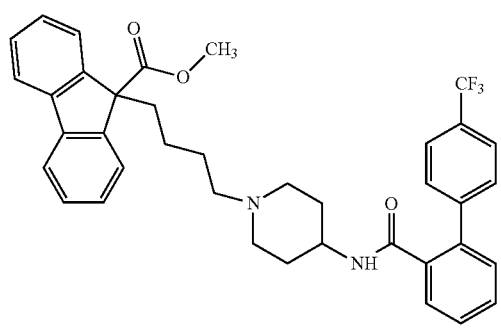 [SMILES: COC(=O)C1(CCCCN2CCC(NC(=O)c3ccccc3-c3ccc(C(F)(F)F)cc3)CC2)c2ccccc2-c2ccccc21] | C |
| 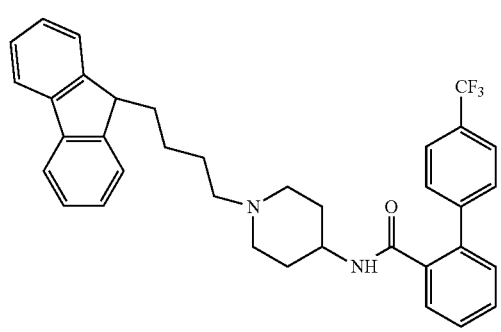 [SMILES: O=C(NC1CCN(CCCCC2c3ccccc3-c3ccccc32)CC1)c1ccccc1-c1ccc(C(F)(F)F)cc1] | D |
-continued
| Structure | Impurity |
|---|---|
| 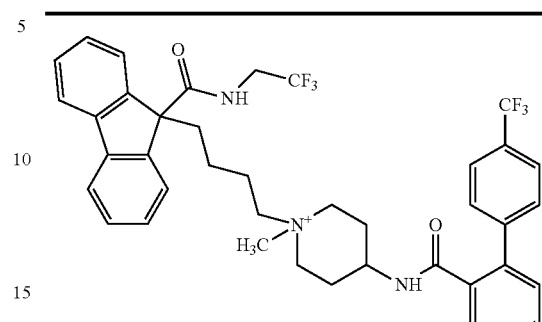 | E |
| 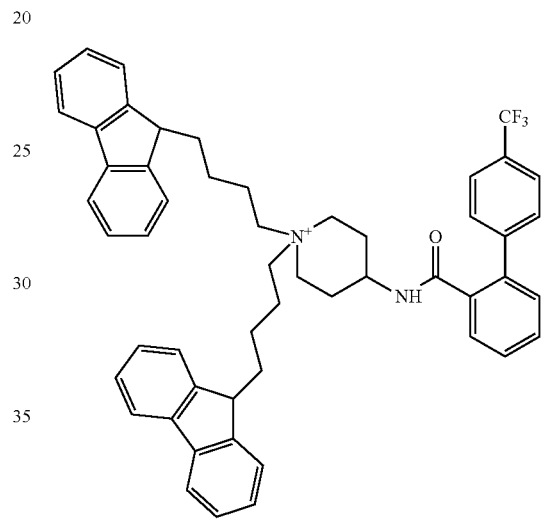 | F |
| 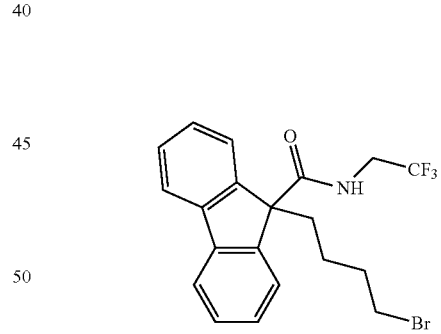 | G |
| 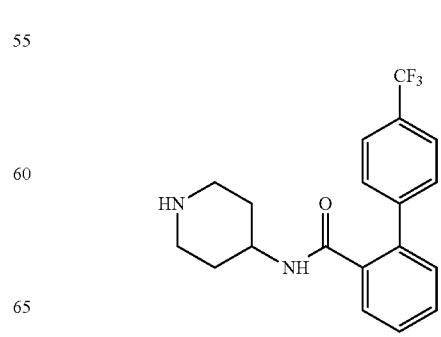 | H |

-continued

| Structure | Impurity |
|---|---|
| 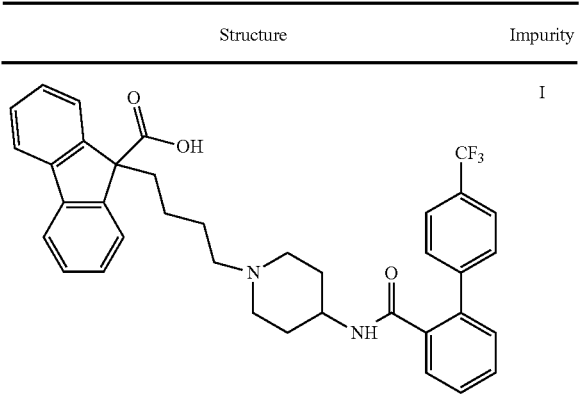 | I |
| 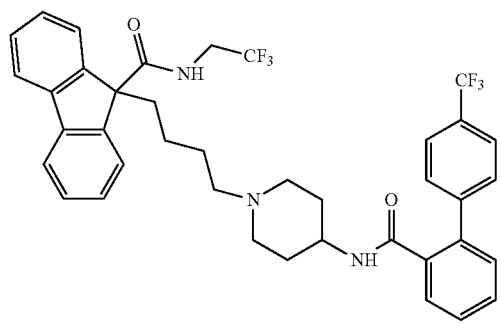 [SMILES: O=C(NC1CCN(CCCCC2(C(=O)NCC(F)(F)F)c3ccccc3-c3ccccc32)CC1)c1ccccc1-c1ccc(C(F)(F)F)cc1] | J |
| 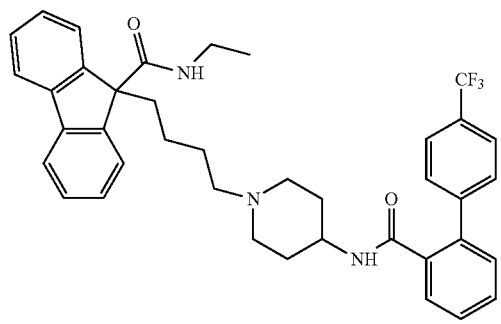 [SMILES: CCNC(=O)C1(CCCCN2CCC(NC(=O)c3ccccc3-c3ccc(C(F)(F)F)cc3)CC2)c2ccccc2-c2ccccc21] | K |
| 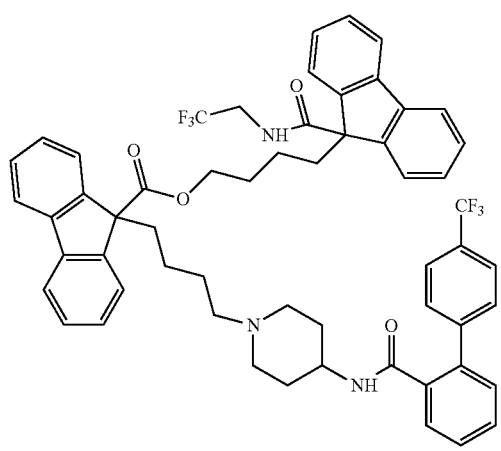 [SMILES: O=C(NC1CCN(CCCCC2(C(=O)OCCCCC3(C(=O)NCC(F)(F)F)c4ccccc4-c4ccccc43)c3ccccc3-c3ccccc32)CC1)c1ccccc1-c1ccc(C(F)(F)F)cc1] | L |

-continued

| Structure | Impurity |
|---|---|
| 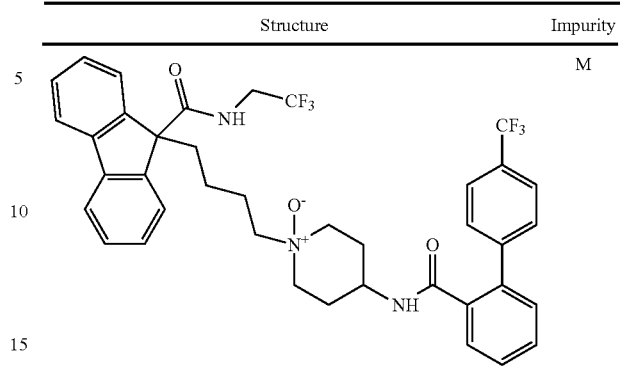 | M |

In one embodiment, the present invention provides lomitapide mesylate with purity greater than 99.5%, as determined by HPLC with conditions as described below:

Apparatus: A High Performance Liquid Chromatograph equipped with quaternary gradient pumps, variable wavelength UV detector attached with data recorder and integrator software.

Column: Inertsil ODS-3 V, 250×4.6 mm, 5μ (Part no. 5020-01802)

Column temperature: 30° C.
Sample Cooler temperature: 15° C.
Mobile Phase:
Mobile phase A=Buffer: Acetonitrile (85:15; v/v)
Buffer: 1 g Potassium dihydrogen phosphate dissolved in 1000 ml water, pH adjusted to 7.0 with 0.5 M Potassium hydroxide solution in water.
Mobile phase B=Acetonitrile:Methanol (50:50, v/v)

| Time (min.) | % Mobile Phase A | % Mobile Phase B |
|---|---|---|
| 0.01 | 70 | 30 |
| 40 | 10 | 90 |
| 60 | 10 | 90 |
| 62 | 70 | 30 |
| 70 | 70 | 30 |

Diluent:Water:Acetonitrile (50:50, v/v)
Flow Rate: 1 mL/minute
Detection: UV 210 nm
Injection Volume: 20 μL The present invention provides a pharmaceutical composition comprising amorphous form of lomitapide mesylate together with one or more pharmaceutically acceptable carriers. The present invention provides a pharmaceutical composition comprising solid dispersion comprising amorphous form of lomitapide mesylate together with one or more pharmaceutically acceptable carriers.

Pharmaceutical composition comprising amorphous form of lomitapide mesylate or solid dispersion comprising amorphous form of lomitapide mesylate includes, but not limited to, solid oral dosage forms such as pellets, powders, granules, tablets, and capsules; liquid oral dosage forms such as suspensions, syrups, dispersions and emulsions; and injectable preparations such dispersions, solutions, and freeze dried compositions. Preferably, the pharmaceutically acceptable composition is a capsule. Pharmaceutically acceptable carriers known in the art may be used in the preparation of the pharmaceutical compositions of the invention.

The examples that follow are provided to enable one skilled in the art to practice the invention and are merely illustrative of the invention. The examples should not be read as limiting the scope of the invention as defined in the features and advantages.

EXAMPLES

Example 1

Preparation of
9-(4-bromobutyl)-9H-fluorene-9-carboxylic acid

To a solution of 9H-fluorene-9-carboxylic acid (200 gm, 0.95 moles) in tetrahydrofuran (8 L) was added n-BuLi (182.7 gm, 2.85 moles, 1.6 M solution in hexane) at about 0-5° C. under nitrogen atmosphere and stirred for about 15 min at same temperature. The temperature of the reaction mass was raised to about 25-30° C. and a solution of 1,4-dibromobutane (246.48 gm, 1.14 moles) in THF (0.5 L) was added. The reaction mass was stirred for about 8-12 hrs at about 25-30° C. After completion of the reaction, pH of the reaction mass was adjusted to about 2-3 with dilute hydrochloric acid and the product was extracted in toluene (4 L). The organic layer was dried under vacuum at about 60-65° C. to afford a residue. The residue was dissolved in diisopropyl ether and the pH was adjusted to about 8-9 with a solution of sodium carbonate in water. The layers were separated and aqueous layer was washed with diisopropyl ether. The aqueous layer was acidified with dilute hydrochloric acid to pH of about 2-3 and the product was extracted with ethyl acetate. The organic layer distilled under vacuum at about 50-55° C. to provide a residue which was stirred with n-heptane. The precipitated solid was filtered and dried under vacuum at about 50-55° C. for 12 hrs to furnish 270 gm of 9-(4-bromobutyl)-9H-fluorene-9-carboxylic acid as pale yellow solid (Yield 82.5%, HPLC purity 96.30%).

Example 2

Preparation of 9-(4-bromobutyl)-N-(2,2,2-trifluoroethyl)-9H-fluorene-9-carboxamide To a solution of 9-(4-bromobutyl)-9H-fluorene-9-carboxylic acid (200 gm, 0.579 moles) in dichloromethane (4 L) was charged N-methyl morpholine (87.88 gm, 0.87 moles). The reaction mass was cooled to about 0-5° C. under nitrogen atmosphere and isobutylchloroformate (102.68 gm, 0.75 moles) was added slowly at about 0-5° C. The reaction mass was stirred for about 15 min at same temperature and a suspension of 2,2,2-trifluoroethylamine hydrochloride (94.2 gm, 0.70 moles) and N-methyl morpholine (87.88 gm, 0.868 moles) in dichloromethane (1 L) was slowly added. The reaction mass was stirred for about 8-12 hrs at room temperature. After completion of the reaction, water was added to the reaction mass at about 25-30° C. and the layers were separated. The organic layer was washed with dilute hydrochloric acid followed by water. The organic layer was distilled off under vacuum at about 35-40° C. to afford a residue. Water was added to the solution of residue in methanol and the obtained mass was stirred. The precipitated solid was filtered and dried under vacuum at about 50-55° C. for about 12 hrs to afford 180 gm of 9-(4-bromobutyl)-N-(2,2,2-trifluroethyl)-9H-fluorene-9-carboxamide as pale yellow solid (Yield 73%, HPLC purity 95.40%).

Example 3

Preparation of 4-trifluoromethyl-biphenyl-2-carboxylic acid(1-benzyl-piperidin-4-yl)-amide A solution of 4'-trifluoromethylbiphenyl-2-carboxylic acid (200 gm, 0.751 moles), 4-aminobenzylpiperidine (142 gm, 0.746 moles), HOBt (120 gm, 0.89 moles), and EDCI-.HCl (143.2 gm, 0.747 moles) in DMF (2 L) was stirred for about 12-15 hrs at about 25-30° C. After completion of the reaction, the reaction mass was slowly added to 10% sodium bicarbonate solution (4 L) under stirring and the precipitated solid was filtered. The solid was slurry washed two times with water and dried at about 60-65° C. in air oven for about 12-15 hrs to afford 320 gm of 4-trifluoromethyl-biphenyl-2-carboxylic acid (1-benzyl-piperidin-4-yl)-amide as a white solid (yield 97.26%, HPLC purity 98.88%)

Example 4

Preparation of N-piperidine-4-yl-4'-(trifluromethyl)-1,1'-biphenyl-2-carboxamide To a solution of 4-trifluoromethyl-biphenyl-2-carboxylic acid (1-benzyl-piperidin-4-yl)-amide (100 gm, 0.22 moles) in methanol (2 L) was added ammonium formate (71.83 gm, 1.14 moles) and 10% palladium carbon (10 gm) at room temperature. The reaction mass was stirred for about 1-2 hrs at reflux temperature. After completion of reaction, the reaction mass was filtered to remove the catalyst. The filtrate was distilled off completely to provide a solid which was washed with diisopropyl ether (100 ml) and slurried with water (100 ml). The obtained solid was dried at about 50-60° C. for about 12-15 hrs to afford N-piperidine-4-yl-4'-(trifluromethyl)-1,1'-biphenyl-2-carboxamide as white solid (yield 95% , purity 99%).

Example 5

Preparation of N-(2,2,2-trifluoroethyl)-9-[4-[4-[[[4'-(trifluoromethyl)[1,1-biphenyl]-2-yl]carbonyl]amino]-1-piperidinyl]butyl]-9H-fluorene-9-carboxamide (Lomitapide)

To a solution of N-piperidine-4-yl-4'-(trifluromethyl)-1,1'-biphenyl-2-carboxamide (150 gm, 0.430 moles) and 9-(4-bromobutyl)-N-(2,2,2-trifluroethyl)-9H-fluorene-9-carboxamide (183.54 gm, 0.430 moles) in dimethyl formamide (750 ml) was added potassium carbonate (148.76 gm, 1.076 moles) and sodium iodide (64.54 gm, 0.43 moles). The reaction mixture stirred for about 8-10 hrs at about 25-30° C. After completion of the reaction, the reaction mass was filtered to remove the inorganic solid. The filtrate was added slowly to water (3750 ml) and stirred for about 2 hrs. The precipitated solid was filtered and dried at about 55-65° C. in air oven for about 12 to 15 hrs to afford crude N-(2,2,2-trifluoroethyl)-9-[4-[4-[[[4'-(trifluoromethyl)[1,1'-biphenyl]-2-yl]carbonyl]amino]-1-piperidinyl]butyl]-9H-fluorene-9-carboxamide (Yield 95-97%, HPLC purity 90-95%). The crude product was purified by crystallization in a mixture of ethanol and water (7:3) to afford pure lomitapide free base (Yield 80-85%, HPLC purity 99.6%). Similar procedure was repeated to prepare second batch of lomitapide free base by using N-piperidine-4-yl-4'-(triflurom-ethyl)-1,1'-biphenyl-2-carboxamide (200 gm, 0.574 moles), 9-(4-bromobutyl)-N-(2,2,2-trifluroethyl)-9H-fluorene-9-carboxamide (237.38 gm, 0.556 moles) in dimethyl formamide (1000 ml) and potassium carbonate (198.34 gm, 1.43 moles), sodium iodide (86.04 gm, 0.574 moles). The crystallization process was carried out as described above to afford lomitapide free base (Yield 80-85%, HPLC purity 99.6%).

XRPD Peaks of Lomitapide Free Base (XRPD Pattern as Per FIG. 3)

| Pos. [°2Th.] | d-spacing [Å] | Rel. Int. [%] |
| --- | --- | --- |
| 2.75 | 32.05 | 0.64 |
| 5.48 | 16.10 | 25.13 |
| 8.28 | 1067 | 0.64 |
| 9.57 | 9.23 | 12.80 |
| 10.95 | 8.07 | 100.0 |
| 11.34 | 7.80 | 1.51 |
| 12.23 | 7.23 | 9.94 |
| 13.46 | 6.57 | 29.49 |
| 13.70 | 6.46 | 63.12 |
| 14.47 | 6.11 | 17.42 |
| 15.78 | 5.61 | 13.80 |
| 16.21 | 5.46 | 22.90 |
| 17.76 | 4.99 | 13.73 |
| 18.19 | 4.87 | 47.59 |
| 18.94 | 4.68 | 36.53 |
| 19.24 | 4.61 | 29.63 |
| 19.89 | 4.46 | 9.66 |
| 20.38 | 4.35 | 19.48 |
| 20.90 | 4.25 | 16.71 |
| 21.48 | 4.13 | 5.72 |
| 21.98 | 4.04 | 27.80 |
| 22.66 | 3.92 | 20.66 |
| 23.67 | 3.75 | 11.97 |
| 24.01 | 3.70 | 6.30 |
| 24.31 | 3.66 | 6.97 |
| 24.93 | 3.57 | 10.55 |
| 25.86 | 3.44 | 4.20 |
| 26.31 | 3.38 | 3.83 |
| 27.60 | 3.23 | 3.55 |
| 28.58 | 3.12 | 9.17 |
| 28.97 | 3.08 | 2.80 |
| 29.53 | 3.02 | 1.10 |
| 30.37 | 2.94 | 4.35 |
| 30.73 | 2.90 | 6.05 |
| 31.46 | 2.84 | 11.89 |
| 32.50 | 2.75 | 1.69 |
| 33.22 | 2.69 | 5.72 |
| 34.04 | 2.63 | 2.80 |
| 34.36 | 2.61 | 2.73 |
| 36.07 | 2.48 | 5.26 |
| 36.76 | 2.44 | 4.27 |
| 37.97 | 2.36 | 0.86 |
| 38.83 | 2.31 | 1.03 |
| 41.85 | 2.15 | 2.38 |
| 42.62 | 2.12 | 3.52 |
| 43.26 | 2.09 | 2.94 |
| 44.52 | 2.03 | 1.78 |
| 47.33 | 1.92 | 0.78 |

Example 6

Preparation of N-(2,2,2-trifluoroethyl)-9-[4-[4-[[[4'-(trifluoromethyl)[1,1'-biphenyl]-2-yl]carbonyl]amino]-1-piperidinyl]butyl]-9H-fluorene-9-carboxamide, methanesulfonate salt (Lomitapide Mesylate)

To a solution of N-(2,2,2-trifluoroethyl)-9-[4-[4-[[[4'-(trifluoromethyl)[1,1'-biphenyl]-2-yl]carbonyl]amino]-1-piperidinyl]butyl]-9H-fluorene-9-carboxamide (1 Kg, 1.44 moles) in ethyl acetate (3 L), methane sulfonic acid (138.54 gm, 1.44 moles) was added slowly and the reaction mass was stirred for about 2 hrs at room temperature. The solution was cooled to about 0-5° C. and stirred for about 12 hrs at same temperature. The precipitated solid was filtered and dried under vacuum at about 60-65° C. to afford amorphous lomitapide mesylate (yield 90-95%, HPLC purity 99.6%; water content by KF method: 1.1%).

Example 7

Preparation of N-(2,2,2-trifluoroethyl)-9-[4-[4-[[[4'-(trifluoromethyl)[1,1'-biphenyl]-2-yl]carbonyl]amino]-1-piperidinyl]butyl]-9H-fluorene-9-carboxamide, methanesulfonate salt (Lomitapide Mesylate)

To a solution of N-(2,2,2-trifluoroethyl)-9-[4-[4-[[[4'-(trifluoromethyl)[1,1'-biphenyl]-2-yl]carbonyl]amino]-1-piperidinyl]butyl]-9H-fluorene-9-carboxamide (1.0 gm, 0.0014 moles) in ethyl acetate (3 ml), methane sulfonic acid (0.14 gm, 0.0014 moles) was added slowly and the reaction mass was stirred for about 2 hrs at room temperature. The solution was distilled under vacuum at about 60-65° C. and the obtained solid was dried under vacuum at about 105° C. for about 24 hrs to afford amorphous lomitapide mesylate (yield 100%, HPLC purity 99.6%).

Example 8

Preparation of N-(2,2,2-trifluoroethyl)-9-[4-[4-[[[4'-(trifluoromethyl)[1,1'-biphenyl]-2-yl]carbonyl]amino]-1-piperidinyl]butyl]-9H-fluorene-9-carboxamide, methanesulfonate salt (Lomitapide Mesylate)

To a solution of N-(2,2,2-trifluoroethyl)-9-[4-[4-[[[4'-(trifluoromethyl)[1,1'-biphenyl]-2-yl]carbonyl]amino]-1-piperidinyl]butyl]-9H-fluorene-9-carboxamide (1.0 gm, 0.0014 moles) in ethyl acetate (3 ml), methane sulfonic acid (0.14 gm, 0.0014 moles) was added slowly and the reaction mass was stirred for about 2 hrs at room temperature. The solution was spray dried at about 60-65° C. and the solid obtained was dried under vacuum at about 105° C. for about 24 hrs to afford amorphous lomitapide mesylate (yield 95%, HPLC purity 99.6%).

Example 9

Preparation of N-(2,2,2-trifluoroethyl)-9-[4-[4-[[[4'-(trifluoromethyl)[1,1'-biphenyl]-2-yl]carbonyl]amino]-1-piperidinyl]butyl]-9H-fluorene-9-carboxamide, methanesulfonate salt (Lomitapide Mesylate)

To a solution of N-(2,2,2-trifluoroethyl)-9-[4-[4-[[[4'-(trifluoromethyl)[1,1'-biphenyl]-2-yl]carbonyl]amino]-1-piperidinyl]butyl]-9H-fluorene-9-carboxamide (1.0 gm, 0.0014 moles) in ethyl acetate (3 ml), methane sulfonic acid (0.14 gm, 0.0014 moles) was added slowly and the reaction mass was stirred for about 2 hrs at room temperature. The solution was distilled under vacuum at about 60-65° C. and the solid obtained was dried under vacuum at about 60-65° C. for about 24 hrs.

The obtained solid was processed in two ways:
(a) The obtained solid was milled and dried under vacuum at about 105° C. for 24 hrs to afford amorphous lomitapide mesylate (yield 90%, HPLC purity 99.6%; water content by KF method: 1.5%).

| | Product (Lomitapide mesylate amorphous form) | | |
|---|---|---|---|
| | d (0.1) | d (0.5) | d (0.9) |
| Before grinding/milling | 3.9 µm | 25.6 µm | 87.4 µm |
| After grinding/milling | 1.4 µm | 13.2 µm | 53.4 µm |

(b) The obtained solid was jet milled and dried under vacuum at 105° C. for 24 hrs to afford amorphous lomitapide mesylate (yield 90% purity 99.6%)

| | Product (Lomitapide mesylate amorphous form) | | |
|---|---|---|---|
| | d (0.1) | d (0.5) | d (0.9) |
| Before grinding/milling | 3.9 µm | 25.6 µm | 87.4 µm |
| After grinding/milling | 1.4 µm | 4.5 µm | 12.9 µm |

Example 10

Preparation of N-(2,2,2-trifluoroethyl)-9-[4-[4-[[[4'-(trifluoromethyl)[1,1'-biphenyl]-2-yl]carbonyl]amino]-1-piperidinyl]butyl]-9H-fluorene-9-carboxamide, methanesulfonate salt (Lomitapide Mesylate)

To a solution of N-(2,2,2-trifluoroethyl)-9-[4-[4-[[[4'-(trifluoromethyl)[1,1'-biphenyl]-2-yl]carbonyl]amino]-1-piperidinyl]butyl]-9H-fluorene-9-carboxamide (1.0 gm, 0.0014 moles) in ethyl acetate (3 ml), methane sulfonic acid (0.14 gm, 0.0014 moles) was added slowly and the reaction mass was stirred for about 2 hrs at room temperature. 3 ml diisopropyl ether was added slowly at room temperature and the solution was stirred for about 5 hrs. The precipitated solid was filtered and dried under vacuum at about 105° C. for about 24 hrs to afford amorphous lomitapide mesylate (yield 90%, HPLC purity 99.3%).

Example 11

Preparation of 9-(4-bromobutyl)-N-(2,2,2-trifluoroethyl)-9H-fluorene-9-carboxamide To a solution of 9-(4-bromobutyl)-9H-fluorene-9-carboxylic acid (35 gm, 0.1 moles) in dichloromethane (0.70 L) was charged N-methyl morpholine (15.38 gm, 0.15 moles). The reaction mass was cooled to 0-5° C. under nitrogen atmosphere and isobutylchloroformate (17.97 gm, 0.13 moles) was added slowly at 0-5° C. The reaction mass was stirred for 30 min at same temperature and 2,2,2-trifluoroethylamine hydrochloride (16.48 gm, 0.12 moles) and N-methyl morpholine (15.38 gm, 0.15 moles) in dichloromethane (70 ml) was added. The reaction mass was stirred for 6 hrs at room temperature and the progress of the reaction was monitored by HPLC. After completion of the reaction, water was added to the reaction mass at 25-30° C. and the layers were separated. The organic layer was washed with dilute hydrochloric acid followed by water and brine solution. The organic layer was distilled off under vacuum at 35-40° C. to afford a residue. The residue was crystallized in ethanol and water mixture 350 ml (7:3). The precipitated solid was filtered dried under vacuum at 50-60° C. for 12 hrs to afford 35 gm of 9-(4-bromobutyl)-N-(2,2,2-trifluroethyl)-9H-fluorene-9-carboxamide as off white solid (Yield 89.4%, HPLC purity 98.03%).

Example 12

Synthesis of 4'-(Trifluoromethyl)biphenyl-2-carboxylic acid

2-Iodobenzoic acid (100 gm, 0.4032 moles), 4-(Trifluoromethyl)phenyl boronic acid (99.55 gm, 0.524 moles), sodium carbonate (164 gm, 1.55 moles) and 20% palladium hydroxide on carbon (15 gm) in water (3.0 L) was heated to 80-90° C. for 6 hrs. The progress of the reaction was monitored by HPLC. After completion of the reaction the reaction mass was cooled 70-80° C. and filtered through hyflow bed. The filtrate was cooled to room temperature and the pH was adjusted to 1-2 with hydrochloric acid. The precipitated solid was filtered and washed with 1.0 L water. The solid was dissolved in 376 ml ethanol at 60-70° C. and charcolised. The solution was filtered through hyflow bed at 60° C. and washed with 180 mL hot ethanol. Water (1.086 L) was added to the filtrate at 50-60° C. and the precipitated solid was cooled to room temperature. The solid was filtered and dried in air oven for 12 hrs at 60° C. to afford 80 gm of 4'-(Trifluoromethyl)biphenyl-2-carboxylic acid as a white solid (Yield 74.55%, HPLC purity 99.98%).

Alternately instead of palladium hydroxide on carbon, palladium (II) acetate can be used in above process.

Example 13

Preparation of 4-trifluoromethyl-biphenyl-2-carboxylic acid(1-benzyl-piperidin-4-yl)-amide A solution of 4'-trifluoromethylbiphenyl-2-carboxylic acid (100 gm, 0.3756 moles), 4-aminobenzylpiperidine (85.77 gm, 0.45 moles), HOBt (63.27 gm, 0.41 moles), and EDCI.HCl (79.2 gm, 0.41 moles) in DMF (1.0 L) was stirred for 10 hrs at 25-30° C. The progress of the reaction was monitored by TLC. After completion of the reaction, the reaction mass was slowly added to 10% sodium bicarbonate solution (2.0 L) under stirring and the precipitated solid was filtered. The solid was slurry washed with 10% sodium bicarbonate solution (2.0 L) followed by 2.0 L water. The solid was dried at 60-65° C. in air oven for 12 hrs to afford 160 gm of crude 4-trifluoromethyl-biphenyl-2-carboxylic acid(1-benzyl-piperidin-4-yl)-amide. The crude material was purified in 25 volume of ethanol water mixture (7:3) at 80-85° C. to afford pure 4-trifluoromethyl-biphenyl-2-carboxylic acid (1-benzyl-piperidin-4-yl)-amide as a white solid (yield 87.8%, HPLC purity 99.82%).

Example 14

Preparation of N-piperidine-4-yl-4'-(trifluromethyl)-1,1'-biphenyl-2-carboxamide:

To a solution of 4-trifluoromethyl-biphenyl-2-carboxylic acid(1-benzyl-piperidin-4-yl)-amide (100 gm, 0.23 moles) in methanol (2.0 L) was added ammonium formate (28.73, 0.46 moles) and charged 5% palladium carbon (15 gm) at room temperature. The reaction mass was stirred for 1-2 hrs at 45-55° C. The progress of the reaction was monitored by TLC. After completion of reaction, reaction mass was filtered through hyflow to remove the catalyst. The filtrate was distilled off completely to provide a solid which was crystallized with diisopropyl ether (500 ml). The obtained solid was dried at 50-60° C. for 12 -15 hrs to afford N-piperidine-4-yl-4'-(trifluromethyl)-1,1'-biphenyl-2-carboxamide as white solid (yield 94.93% , purity 99.42%).

Example 15

Preparation of N-(2,2,2-trifluoroethyl)-9-[4-[4-[[[4'-(trifluoromethyl)[1,1'-biphenyl]-2-yl]carbonyl]amino]-1-piperidinyl]butyl]-9H-fluorene-9-carboxamide, methanesulfonate salt (Lomitapide Mesylate)

To a solution of N-(2,2,2-trifluoroethyl)-9-[4-[4-[[[4'-(trifluoromethyl)[1,1'-biphenyl]-2-yl]carbonyl]amino]-1-piperidinyl]butyl]-9H-fluorene-9-carboxamide (250 gm, 0.36 moles) in ethyl acetate (750 ml) was added methane sulfonic acid (34.63 gm, 0.36 moles) slowly and the reaction mass was stirred for 30 min at 10-15° C. to get a clear solution. The solution was added to n-heptane (3.75 L). The precipitated solid was filtered and dried under vacuum at 80-85° C. and jet milled to afford amorphous lomitapide mesylate as white solid (yield 96%; HPLC purity 99.74%).

Use of a non-hydroxylic solvent ensures absence of genotoxic alkyl mesylates which would be generated if an alcoholic solvent was used in this step.

Comparative Example 1

Preparation of Lomitapide Mesylate by Using Alcoholic Solvent 10 gm lomitapide was dissolved in 50 ml isopropyl alcohol and 1.3 gm methane sulfonic acid was added at room temperature. To this mixture was added 100 ml heptane and maintained for 1 hr. The solvent was distilled off under vacuum at below 45° C. to obtain a residue which was taken in 100 ml heptane and stirred for 4 hrs at room temperature. The precipitated solid was filtered and dried under vacuum to afford 3 gm of amorphous Lomitapide mesylate.

If this sample would be subjected to GCMS analysis, it would show substantial content of isopropyl mesylate (a genotoxic impurity).

Comparative Example 2

Preparation of Lomitapide Mesylate Using Alcoholic Solvent

Lomitapide (4.5 gm) was dissolved in methanol (20 ml) and the reaction mass was cooled to −5° C. to 5° C. To this reaction mixture methanesulfonic acid (0.5 ml) was then added at −5° C. to 5° C. and maintained for 30-45 minutes. The reaction mixture then distilled at 30-40° C. and the solid was dried to yield 5 gm of lomitapide mesylate.

Content of methyl mesylate by GCMS in lomitapide mesylate: 338.48 ppm.

Example 16

Preparation of Amorphous Co-Precipitate of Lomitapide Mesylate with Mannitol 0.14 gm (0.0014 mmol) methane sulfonic acid was added to 1 gm (0.0014 mmol) lomitapide in 100 ml of N,N-dimethyl formamide and the solution was stirred for 15 minutes. To this solution 1 gm mannitol was added and heated to 125° C. to get clear solution and then stirred for another 15 minutes. The clear solution was distilled out completely under vacuum at 65-70° C. to afford 3 gm co-precipitate of lomitapide mesylate with mannitol.

Example 17

Preparation of Amorphous Co-Precipitate of Lomitapide Mesylate with Lactose 0.14 gm (0.0014 mmol) methane sulfonic acid was added to 1 gm (0.0014 mmol) lomitapide in 10 ml of N,N-dimethyl formamide and the solution was stirred for 15 minutes. To this solution 1 gm lactose was added and heated to 140° C. to get clear solution and then stirred for another 15 minutes. The clear solution was distilled out completely under vacuum at 65-70° C. to afford 3 gm co-precipitate of lomitapide mesylate with lactose.

Example 18

Preparation of Amorphous Co-Precipitate of Lomitapide Mesylate with Syloid 0.14 gm (0.0014 mmol) methane sulfonic acid was added to 1 gm (0.0014 mmol) lomitapide in 5 ml ethyl acetate and the solution was stirred for 15 minutes. To this solution 1 gm syloid was added and stirred for another 15 minutes at 25-30° C. The solution was distilled out completely under vacuum at 60-65° C. to afford 3 gm co-precipitate of lomitapide mesylate with syloid.

Example 19

Preparation of Amorphous Co-Precipitate of Lomitapide Mesylate with Microcrystalline Cellulose 0.14 gm (0.0014 mmol) methane sulfonic acid was added to 1 gm (0.0014 mmol) lomitapide in 5 ml ethyl acetate and the solution was stirred for 15 minutes. To this solution 1 gm microcrystalline cellulose was added and stirred for another 15 minutes at 25-30° C. The solution was distilled out completely under vacuum at 60-65° C. to afford 3 gm co-precipitate of lomitapide mesylate with microcrystalline cellulose.

Example 20

Capsule Containing 5 mg of Lomitapide

Capsule containing 5 mg of Lomitapide are produced from the following ingredients.

| Component | 5 mg capsule Amount (mg/capsule) |
|---|---|
| Lomitapide mesylate amorphous (as per example 15) | 5.70 mg (5.0 mg free base) |
| Pregelatinized Starch | 5.0 mg |
| Microcrystalline Cellulose | 10.0 mg |
| Lactose monohydrate | 73.0 mg |
| Sodium Starch Glycolate | 5.0 mg |
| Colloidal Silicon Dioxide | 1.0 mg |
| Magnesium Stearate | 0.3 mg |
| Purified water USP | q.s. |
| Total Amount | 100 mg |

The Lomitapide mesylate and colloidal silicon dioxide are blended in a suitable blender with lactose monohydrate, microcrystalline cellulose, pregelatinized starch and a portion of sodium starch glycolate. The resulting blend is wet granulated with water. The wet granulation is dried in a suitable dryer. The remaining portion of sodium starch glycolate is added to the granulation and mixed therein. Magnesium stearate is added to the granulation and mixed therein. The resulting blend is filled into capsules.

The invention claimed is:

1. A process for the preparation of an amorphous form of lomitapide mesylate free of alkyl mesylates comprising
   (a) providing a solution of lomitapide mesylate in a non-hydroxylic solvent; and
   (b) isolating the amorphous form of lomitapide mesylate by
      combining the solution obtained in (a) with an antisolvent followed by optional cooling to precipitate amorphous form of lomitapide mesylate, wherein the amorphous form of lomitapide mesylate has purity greater than 99.5% and a DSC endothermic peak at about 113±3° C. as shown in FIG. 2; wherein the non-hydroxylic solvent is ethyl acetate and the antisolvent is heptane.

2. The process as claimed in claim 1, wherein the lomitapide mesylate in step (a) is prepared by treating lomitapide with methane sulfonic acid.

3. Lomitapide mesylate free of alkyl mesylates in amorphous form wherein the amorphous form of lomitapide mesylate has purity greater than 99.5% and has a DSC endothermic peak at about 113±3° C., prepared by a process of claim 1.

4. The process as claimed in claim 2, wherein the lomitapide treated with methanesulfonic acid is a crystalline lomitapide characterized by an X-ray powder diffraction (XRPD) spectrum having peak reflections at about 10.9, 13.7, 18.1, 18.9 and 21.9±0.2 degrees 2 theta.

* * * * *